United States Patent [19]

Flury et al.

[11] Patent Number: 5,352,831
[45] Date of Patent: Oct. 4, 1994

[54] OLIGOMERIC CYANOGUANIDINES

[75] Inventors: Peter Flury, Himmelried; Martin Roth, Giffers; Sameer H. Eldin, Fribourg, all of Switzerland

[73] Assignee: Ciba-Geigy Corporation, Ardsley, N.Y.

[21] Appl. No.: 914,158

[22] Filed: Jul. 14, 1992

Related U.S. Application Data

[63] Continuation-in-part of Ser. No. 234,778, Aug. 22, 1988, abandoned.

[30] Foreign Application Priority Data

Sep. 2, 1987 [CH] Switzerland ............ 3358/87-2

[51] Int. Cl.$^5$ .................................. C07C 279/28
[52] U.S. Cl. .................................. 564/104; 546/256; 546/264; 546/268; 546/278; 546/281; 546/283; 546/284; 546/306; 548/311.1; 548/312.7; 548/313.1; 548/314.7; 548/315.1; 548/315.4; 548/326.5; 548/332.5; 548/517; 548/518; 548/527; 548/557; 548/558; 549/59; 549/60; 549/68; 549/414; 549/415; 549/424; 549/472; 549/480
[58] Field of Search ............ 548/557, 234, 337.1, 548/191; 560/107; 564/104, 230, 233, 236, 252; 549/28, 68, 419, 480; 544/53, 59, 60, 88, 120, 129, 146, 147, 149, 155, 154, 323, 382; 546/229, 306; 524/186

[56] References Cited

U.S. PATENT DOCUMENTS

| | | | |
|---|---|---|---|
| 3,864,313 | 2/1975 | Susman | 260/75 |
| 4,487,964 | 12/1984 | Watson, Jr. et al. | 564/252 |
| 4,568,694 | 2/1986 | Griffin et al. | 564/104 X |

FOREIGN PATENT DOCUMENTS

| | | |
|---|---|---|
| 2734777 | 7/1977 | Australia . |
| 126567 | 5/1984 | European Pat. Off. . |
| 2733952 | 2/1978 | Fed. Rep. of Germany . |
| 60-127346 | 7/1985 | Japan . |
| 61-207425 | 9/1986 | Japan . |
| 80483 | 3/1990 | Japan . |
| 930036 | 5/1961 | United Kingdom . |

OTHER PUBLICATIONS

Lee, et al., Handbook of Epoxy Resins (New York, McGraw-Hill Books, 1985) pp. 10-16.
Masters, et al, Synthesis, 1980, pp. 755-756.
Ashida et al. Chem. Abs. vol. 114, 1991 Abstract 63778c (Abstract for JP 80483).
Mitsubishi, Chemical Abstracts vol. 104, 1986 Abstract 34891x (Abstract for JP 60127346).
Derwent Abstract of JP Sho 6044543A (1985).

*Primary Examiner*—Richard L. Raymond
*Attorney, Agent, or Firm*—Michele A. Kovaleski; Luther A. R. Hall; JoAnn Villamizar

[57] ABSTRACT

Oligomeric cyanoguanidines of formula I

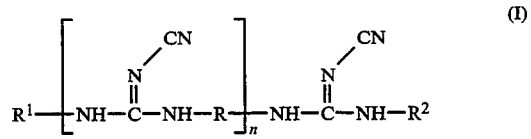

wherein, for example, $R^1$ and $R^2$ are each phenyl, R is 1,4-phenylene and n is an integer from 1 to 20, are suitable latent hardeners for epoxy resins. They are readily soluble in solvents suitable for the application of epoxy resins, and the cured products obtained therewith have a high glass transition temperature.

8 Claims, No Drawings

OLIGOMERIC CYANOGUANIDINES

This is a continuation-in-part of patent application Ser. No. 234,778 filed Aug. 22, 1988, now abandoned.

The present invention relates to oligomeric cyanoguanidines, to a process for their preparation, and to the use thereof as latent hardeners for epoxy resins.

Dicyandiamide has long been successfully used as latent hardener for epoxy resins (q.v. H. Lee and K. Neville, "Handbook of Epoxy Resins", McGraw Hill, New York, 1982, p. 10–16) and is used in practice in particular as hardener for solid laminating resins. However, dicyandiamide has the serious drawback that it is only soluble in solvents which are unsuitable for the laminating industry, for example in water, acetone/water, methanol, N-methylpyrrolidone, dimethyl formamide, hydroxylated ethers and the like. The solvent commonly used at the present time, 2-methoxyethanol, is problematical for toxicological reasons. In addition, epoxy resins cured with dicyandiamide have comparatively low glass transition temperatures.

The oligomeric cyanoguanidines of this invention are, like dicyandiamide, latent hardeners which are stable at room temperature, but effect rapid crosslinking of the resins at elevated temperature. They are readily soluble in uproblematical solvents suitable for the application of epoxy resins. In addition, the epoxy resins cured with them have a substantially higher glass transition temperature than systems cured with dicyandiamide.

Specifically, the invention relates to oligomeric cyanoguanidines of formula I

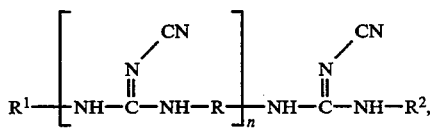

wherein R is a divalent $C_2$–$C_{20}$aliphatic, mono- or polynuclear $C_5$–$C_{20}$-cycloaliphatic, $C_6$–$C_{20}$aromatic or a saturated or unsaturated 5- or 6-membered heterocycle radical which contains one or two O, S or N atoms or a group of formula II

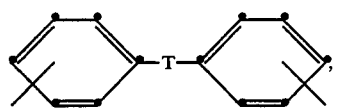

wherein T is methylene, isopropylidene, CO, O, S or $SO_2$, $R^1$ and $R^2$ are each independently of the other a $C_1$–$C_{12}$alkyl, $C_5$–$C_{10}$cycloalkyl, $C_6$–$C_{10}$-aryl, $C_7$–$C_{12}$aralkyl or a saturated or unsaturated monovalent 5- or 6-membered heterocycle radical which contains one or two O, S or N atoms, and n is an integer from 1 to 20, which radicals R, $R^1$ and $R^2$ are unsubstituted or are substituted by $C_1$–$C_4$alkyl, $C_1$–$C_4$alkoxy, nitro, halogen, $R^3$OCO or $R^3$COO, and $R^3$ is phenyl or $C_1$–$C_4$alkyl, with the proviso that 1,6-hexane-bis(3-cyano-2-isobutyl-guanidine) and 1,8-bis[N'-(3-(2-thiazolyl)-propyl)-N"-cyanoguanidino]-octane are excluded.

The structure of the cyanoguanidines of formula I has, for simplicity's sake, been illustrated as 2-cyanoguanidine (i.e. with the cyano group attached to the =N-nitrogen atom). It will be self-evident that these compounds may also be in the form of tautomers, i.e. as 1- or 3-cyanoguanidines, and that the position of equilibrium between the possible tautomers depends on the radicals $R^1$, $R^2$ and R.

Monomeric cyanoguanidines of the type

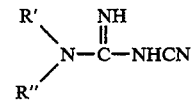

are known hardners for acetal resins or polyurethane resins, as disclosed, for example, in Japanese patent Kokai Sho-60-44543 (1985) and in U.S. Pat. No. 3,864,313. The curable acetal compositions disclosed in the above mentioned Japanese patent publication additionally contain small amounts of a polyglycidyl ether or a diglycidyl ester to improve the adhesion of the polyacetal resin and the inorganic fillers present therein.

Japanese patent Kokai Sho-61-207425 (1986) discloses the use of mixtures of monomeric cyanoguanidines, in particular dicyandiamide, polyether-polyamines and substituted guanidines as hardners for special epoxy resins. These hardener mixtures are not suitable as latent hardeners and the epoxy resins cured with them have, in addition, comparatively low glass transition temperatures.

The compounds of this invention can be prepared by heating a mixture containing a monoisocyanate $R^1$—NCO and/or $R^2$—NCO and a diisocyanate OCN-R-NCO, in the presence of a catalyst, to give an oligomeric carbodiimide of formula III

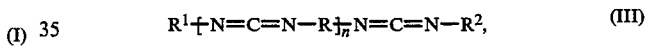

wherein $R^1$, $R^2$, R and n are defined above, asequently reacting said carbodiimide of formula III with cyanamide. The present invention also relates to the above preparatory process.

The starting mono- and diisocyanates are known and can be prepared in known manner.

The catalytic reaction of isocyanates to carbodiimides is likewise known and is described, for example, by S. R. Sandler and W. Karo in "Organic Functional Group Preparation", Vol. 2 (Organic Chemistry Series, Vol. 12-2), Academic Press, Orlando, Fla., USA, 1986, pp. 233–258. Examples of suitable catalysts are metal alcoholates and metal phenolates such as potassium tert-butylate, sodium phenolate or titanium isopropylate, metal carbonyls such as $Fe(CO)_5$, $W(CO)_6$ or $Mo(CO)_6$ and, in particular, specific phosphorus compounds such as phosphonium salts or phosphine oxides. Particularly suitable catalysts are 5-membered cyclic phosphine oxides, for example 1-ethyl-3-methyl-1-phospha-3-cyclopentene-1-oxide and, in particular, 3-methyl-1-phenyl-1-phospha-3-cyclopentene-1-oxide. The amount of catalyst is preferably ca. 0.1 to 2 mol %, most preferably 0.3 to 1 mol%, based on the reactants.

The reaction is conveniently carried out in an inert solvent such as toluene, xylene, cyclohexane, $CCl_4$ and the like, at elevated temperature, for example above 30° C., preferably in the range from 40° to 150° C., for example under reflux.

Depending on the ratio of the monoisocyanate to the diisocyanate, oligomeric carbodiimides of formula III with different molecular weight distribution are obtained. In general, the reaction yields a mixture of oligomers whose average molecular weight can be controlled, if required, by addition of more or less diisocyanate to the monocyanate. It is, however, also possible to prepare selectively products having a substantially uniform molecular weight. The use of about 0.5 to 10 moles, preferably about 1 to 6 moles, of monoisocyanate per mole of diisocyanate has proved particularly suitable.

The second step of the synthesis, the addition of cyanamide to the oligomeric carbodiimide, is normally carried out without changing the degree of polymerisation. The reaction is preferably carried out in the presence of a basic catalyst, for example a tertiary amine such as triethylamine, in an inert solvent such as diethyl ether, tetrahydrofuran, dioxane or, preferably, in a protic solvent such as isopropanol, at normal or elevated temperature.

Preferred oligomeric cyanoguanidines of formula I are those wherein n is an integer from 1 to 10, preferably from 1 to 5.

The invention further relates to mixtures of cyanoguanidines obtainable by heating a mixture containing a monoisocyanate $R^1$—NCO and/or $R^2$—NCO and a diisocyanate OCN—R—NCO, in the presence of a catalyst, to give a carbodiimide or formula III*

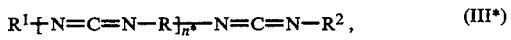

$$R^1 + N = C = N - R \overline{)_{n^*}} N = C = N - R^2, \quad (III^*)$$

wherein $R^1$, $R^2$ and R have the given meanings and $n^*$ is 0 or an integer from 1 to 20, and subsequently reacting said carbodiimide of formula III* with cyanamide.

The radical R in compounds of formula I can be a divalent straight chain or branched aliphatic radical of 2 to 20, preferably 2 to 10 and, most preferably, 2 to 6, carbon atoms. Examples of suitable aliphatic radicals R are ethylene, 1,2- and 1,3-propylene, butylene, pentamethylene and hexamethylene, heptylene, octylene, decylene, dodecylene, hexadecylene and neopentylene.

R can also be a mononuclear or polynuclear cycloaliphatic divalent radical of 5 to 20 carbon atoms, for example cyclopentylene, cyclohexylene, cycloheptylene, cyclooctylene, bis(cyclohexylene)methane, 2,2-bis(cyclohexylene)propane, decalinylene or the radical obtained after eliminating the two amino groups of isophoronediamine.

An aromatic radical R is preferably 1,3- or 1,4-phenylene or naphthylene, each of which, if desired, may also be substituted, for example, by one or more $C_1$–$C_4$alkyl groups such as methyl, ethyl or propyl, the corresponding alkoxy, alkoxycarbonyl or alkanoyloxy groups, or by halogen atoms, preferably chlorine or bromine, or nitro groups. The cited groups are preferably unsubstituted or substituted by a methyl or methoxy group. Particularly preferred aromatic radicals are 1,3- and 1,4-phenylene groups.

The aliphatic and cycloaliphatic radicals cited above as well as the heterocyclic radicals R can also contain the substituents mentioned for the aromatic radicals R.

Particularly suitable heterocyclic radicals R are saturated or unsaturated 5- or 6-membered heterocycles which contain one or two O, S or N atoms, for example divalent radicals of furan, pyran, pyridine, pyrrole, imidazole, thiophene and the like.

Particularly preferred compounds of formula I are those wherein R is an aliphatic radical of 2 to 10 carbon atoms, a cycloaliphatic radical of 5 or 6 carbon atoms or an aromatic radical of 6 to 10 carbon atoms, or is a group of formula II, wherein T is methylene or isopropylidene.

R as a group of formula II is preferably bound in 4,4'-position.

$R^1$ and $R^2$ may each independently of the other be a branched or preferably straight chain alkyl group of 1 to 12, preferably 1 to 6 and, most preferably, 1 or 2, carbon atoms, Examples of such alkyl groups are dodecyl, decyl, octyl, heptyl, butyl, propyl and, preferably, ethyl or methyl.

$R^1$ and/or $R^2$ as cycloalkyl is preferably cyclopentyl or cylcohexyl, each of which may be substituted by one or more $C_1$–$C_4$alkyl groups. These groups are preferably unsubstituted.

$R^1$ and/or $R^2$ as aryl is preferably phenyl, tolyl, methoxyphenyl or naphthyl. Aralkyl of 7 to 12 carbon atoms is suitably benzyl or naphthylmethyl.

$R^1$ and/or $R^2$ as a heterocyclic radical of 4 to 8 carbon atoms may suitably be one of the heterocycles mentioned as possible groups R, but in this case as monovalent radical.

Preferred cyanoguanidines of formula I are those wherein $R^1$ and $R^2$ are each independently of the other $C_1$–$C_6$alkyl, $C_5$–$C_6$cycloalkyl, $C_6$–$C_{10}$aryl or benzyl.

Especially preferred compounds of this invention are those compounds wherein R is phenylene, methylphenylene, the radical

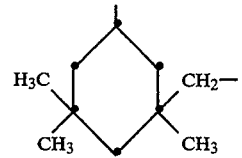

or a group of formula II, wherein T is methylene, and $R^1$ and $R^2$ are each independently of the other phenyl, tolyl, methoxyphenyl, naphthyl or cyclohexyl.

In general, those oligomeric cyanoguanidines are preferred in which all three radicals R, $R^1$ and $R^2$ are groups of the same kind, for example compounds wherein each of these groups is a cycloaliphatic radical or each is an aromatic radical.

Still more preferred are cyanoguanidines of formula I, wherein R, $R^1$ and $R^2$ are aromatic radicals.

The most preferred compounds of formula I are those wherein R is methylphenylene or a group of formula II, in which T is methylene, and $R^1$ and $R^2$ are each phenyl.

The cyanoguanidines and mixtures thereof of this invention are suitable latent hardeners for epoxy resins. Accordingly, the invention also relates to curable compositions comprising (a) an epoxy resin and (b) an oligomeric cyanoguanidine of formula I, or a mixture of such cyanoguanidines, as hardener.

Suitable epoxy resins (a) are all those which can be cured with the cyanoguanidines of this invention. Such epoxy resins are for example: alicyclic polyepoxides such as epoxyethyl-3,4-epoxycyclohexane (vinylcyclohexene diepoxide), limonene diepoxide, dicyclopentadiene diepoxide, bis(3,4-epoxycyclohexylmethyl) adipate, 3',4'-epoxycyclohexylmethyl-3,4-epoxycyclohexane carboxylate, 3',4'-epoxy-6'-methylcyclohexylmethyl-3,4-epoxy-6-methylcyclohexane carboxylate, 3-(3',4'-epoxycyclohexyl)-2,4-dioxaspiro[5,5]-8,9-epoxyundecane, 3-glycidoxyethoxyethyl-2,4-dioxaspiro[5,5]-8,9-epoxyundecane;

di- or polyglycidyl ethers of polyhydric alcohols such as 1,4-butanediol or of polyalkylene glycols such as polypropylene glycols, di- or polyglycidyl ethers of cycloaliphatic polyols such as 2,2-bis(4-hydroxycyclohexyl)propane, di- or polyglycidyl ethers of polyhydric phenols such as resorcinol, bis(p-hydroxyphenyl)methane (bisphenol F), 2,2-bis(p-hydroxyphenyl)propane (bisphenol A), 2,2-bis(4'-hydroxy-3',5'-dibromophenyl)propane, 1,1,2,2-tetrakis(p-hydroxyphenyl)ethane, or of condensation products of phenols with formaldehyde, e.g. phenol and cresol novolaks, which condensation products are obtained under acid conditions; and also di- or poly($\beta$-methylglycidyl) ethers of the above polyalcohols and polyphenols;

polyglycidyl esters and poly($\beta$-methylglycidyl) esters of polyvalent carboxylic acids such as phthalic acid, terephthalic acid, tetrahydrophthalic acid and hexahydrophthalic acid;

N-glycidyl derivatives of amines, amides and heterocyclic nitrogen bases, e.g. N,N-diglycidylaniline, N,N-diglycidyltoluidine, N,N,N',N'-tetraglycidylbis(p-aminophenyl),methane, triglycidylisocyanurate, N,N'-diglycidylethyleneurea, N,N'-diglycidyl-5,5-dimethylhydantoin, N,N'-di-glycidyl-5,5-dimethyl-6-isopropyl-5,6-dihydrouracil.

If desired, active diluents can be added to the curable compositions in order to reduce the viscosity. Examples of such diluents are: styrene oxide, butyl glycidyl ether, 2,2,4-trimethylpentyl glycidyl ether, phenyl glycidyl ether, cresyl glycidyl ether, glycidyl esters of synthetic, highly branched, mainly tertiary, aliphatic monocarboxylic acids.

In addition, curing accelerators can be used in the curing. Examples of such accelerators are: tertiary amines, the salts or quaternary ammonium compounds thereof, e.g. benzyldimethylamine, 2,4,6-tris(dimethylaminomethyl)phenol, 1-methylimidazole, 2-ethyl-4-methylimidazole, N-acylimidazoles, for example the compounds described in U.S. Pat. Nos. 4,436,892 and 4,587,311, 4-aminopyridine, tripentylammonium phenolate; or alkali metal alcoholates, e.g. sodium hexane triolate.

Curable compositions of this invention are preferred which, in addition to containing components (a) and (b), contain a curing accelerator (c), preferably an imidazole derivative.

The components (a), (b) and (c) employed in the curable compositions of this invention may be individual compounds or mixtures.

The curable compositions of this invention preferably contain 5 to 25% by weight, most preferably 10 to 15% by weight, of component (b) and, optionally 0.05 to 5% by weight, preferably 0.1 to 1% by weight, of the accelerator (c), based on the amount of (a)+(b).

The invention further relates to the use of the curable compositions for the preparation of crosslinked products.

Curing of the mixtures of the invention is conveniently carried out in the temperature range from 100° to 300° C., preferably from 120° to 250° C. Curing can be carried out in known manner in two or more steps, the first curing step being effected at low temperature and the post-curing at more elevated temperature.

If desired, curing can be carried out in two steps such that the curing reaction is first prematurely discontinued or the first step is carried out at slightly elevated temperature to give a still fusible and/or soluble curable precondensate (B-stage) from the epoxy component (a) and the hardener (b). Such a precondensate can be used, for example, for the preparation of prepregs, moulding compounds or fluidized powders.

The term "curing" as employed herein means the conversion of the soluble, either liquid or fusible polyepoxide into solid, insoluble and infusible three-dimensional crosslinked products or moulding materials, normally accompanied by simultaneous shaping to moulded articles such as castings, mouldings and laminated materials, and to impregnations, coatings, films or bonds.

The compositions of this invention are particularly suitable for use as laminating resins for the preparation of prepregs and fibre-reinforced composites.

The following Examples illustrate the invention in more detail.

Preparatory Examples

EXAMPLE 1

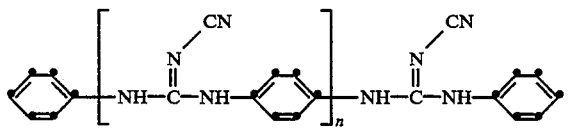

A 250 ml three-necked round flask equipped with stirrer, thermometer, reflux condenser as well as drying tube and bubble counter, is charged with:

40.0 g (336 mmol) of phenyl isocyanate
10.0 g (62.6 mmol) of 1,4-phenylene diisocyanate
0.5 g (2.6 mmol) of 3-methyl-1-phenyl-1-phospha-3-cyclopentene-1-oxide, and
100 ml of toluene.

This solution is stirred for 2 hours under reflux, with evolution of $CO_2$. The solvent is then removed on a rotary evaporator and to the residue (yellowish oil) are added:

100 ml of isopropanol
33.6 g (800 mmol) of cyanamide, and
2.0 ml of triethylamine.

The reaction mixture is stirred for 2 hours at 70°–80° C., then cooled with an ice bath to ca. 10° C. The precipitate is isolated by filtration, washed with isopropanol and dried under vacuum, affording 41.0 g of a white powder with a softening point of 109°–118° C.

EXAMPLE 2

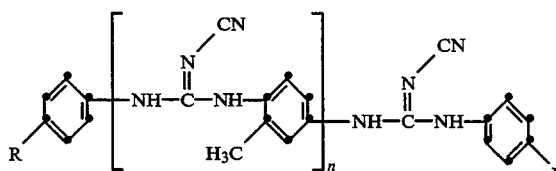

R = H or $OCH_3$

A 1 liter three-necked round flask equipped with stirrer, thermometer, reflux condenser as well as drying tube and bubble counter, is charged with:

85.0 g (714 mmol) of phenyl iso0 g (570 mmol) of p-methoxyphenyl isocyanate
42.5 g (244 mmol) of 4-methyl-m-phenylene diisocyanate 2.0 g (10.4 mmol) of 3-methyl-1-phenyl-1-phospha-3-cyclopentene-1-oxide, and
400 ml of toluene.

This solution is stirred for 2 hours under reflux, with evolution of $CO_2$. The solvent is then removed on a rotary evaporator. To the residue (yellowish oil) are added:
400 ml of isopropanol
128 g (3030 mmol) of cyanamide, and
8 ml of triethylamine.

The reaction mixture is stirred for 2 hours at 70°–80° C., then cooled with an ice bath to ca. 10° C. The precipitate is isolated with filtration, washed with isopropanol and dried under vacuum, affording 219 g of a colourless powder with a softening point of 110°–125° C.

EXAMPLE 3

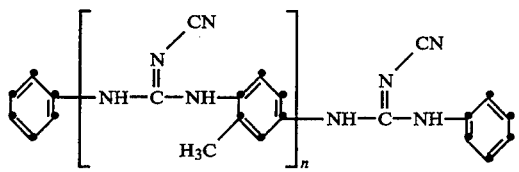

A 2 liter three-necked round flask equipped with stirrer, thermometer, reflux condenser as well as drying tube and bubble counter, is charged with:
240.0 g (2.01 mol) of phenyl isocyanate
160.0 g (0.919 mol) of 4-methyl-m-phenylene diisocyanate
2.0 g (0.001 mol) of methyl-1-phenyl-1-phospha-3-cyclopentene-1-oxide, and
900 ml of toluene.

This solution is worked up as described in Example 1. To the residue are added:
1200 ml of isopropanol
246.0 g (5.86 mol) of cyanamide, and
15.0 g of triethylamine.

Working up is as described in Example 1. Yield: 458 g of a yellowish powder with a softening point of 175°–180° C.

Elemental analysis: (%) C 53.6; H 5.6; N 37.5.

Example 4

A 250 ml three-necked round flask equipped with stirrer, thermometer, reflux condenser as well as drying tube and bubble counter, is charged with:
15.0 g (126 mmol) of phenyl isocyanate
15.0 g (113 mmol) of p-tolylisocyanate
20.0 g (115 mmol) of 4-methyl-m-phenylene diisocyanate
0.5 g (2.6 mmol) of 3-methyl-1-phenyl-1-phospha-3-cyclopentene-1-oxide and
100 ml of toluene.

This solution is worked up as described in Example 1. To the residue are added:
100 ml of isopropanol
38.0 g (905 mmol) of cyanamide, and
2 ml of triethylamine.

The reaction mixture is stirred for 2 hours at 70°–80° C., then cooled with an ice bath to ca. 10° C. The precipitate is isolated by filtration, washed with isopropanol and dried under vacuum, affording 47.4 g of a colourless powder with a softening range of 180°–185° C.

EXAMPLE 5

In this experiment, the same reactants as in Example 3 are reacted, but the final product is isolated in a different manner. A 250 ml three-necked round flask equipped with stirrer, thermometer, reflux condenser as well as drying tube and bubble counter, is charged with:
30.0 g (252 mmol) of phenyl isocyanate
20.0 g (115 mmol) of 4-methyl-m-phenylene diisocyanate
0.5 g (2.6 mmol) of 3-methyl-1-phenyl-1-phospha-3-cyclopentene-1-oxide, and
100 ml of toluene.

This solution is worked up as described in Example 1. The resultant carbodiimide mixture has a molecular weight of $\overline{M}_n=318$ and $\overline{M}_w=469$, determined by gel permeation chromatography (THF, polystyrene standard). To this mixture are added:
120 ml isopropanol
80 ml of tetrahydrofuran
2 ml of triethylamine, and
19 g (452 mmol) of cyanamide.

The reaction mixture is stirred for 2 hours at 70°–80° C., then poured into 500 ml of water. The precipitate is isolated by filtration and dried under vacuum, affording 48.0 g of a slightly yellowish powder with a softening range of 147°–164° C.

Elemental analysis: (%): C 65.66; H 5.09; N 28.22.

EXAMPLE 6

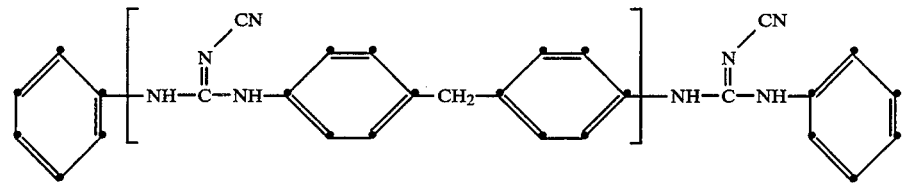

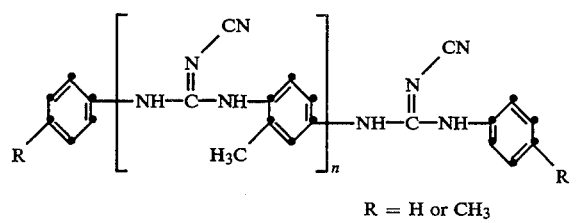

R = H or CH₃

A 250 ml three-necked round flask equipped with stirrer, thermometer, reflux condenser as well as drying tube and bubble counter, is charged with:
35.0 g (294 mmol) of phenyl isocyanate
15.0 g (60 mmol) of diphenylmethane-4,4'-diisocyanate
0.1 g (0.52 mmol) of 3-methyl-1-phenyl-1-phospha-3-cyclopentene-1-oxide, and 100 ml of toluene.
This solution is worked up as described in Example 1. A solution consisting of
100 ml of 1-methoxy-2-propanol
15.0 g (537 mmol) of cyanamide, and
0.5 ml of triethylamine
is added dropwise to the residue over 1 hour at room temperature. During this addition the temperature rises to 45° C. After stirring for 4 hours at room temperature, the reaction solution is poured into 300 ml of water. The precipitate is isolated by filtration, washed with water and dried under vacuum, affording 48.1 g of a colourless powder with a softening range of 162°–169° C.

Use Examples

A₁) 10 parts of the hardener prepared according to Example 3 are mixed with 90 parts of bisphenol A diglycidyl ether (epoxy value: 4.5 eq/kg). When this mixture is heated, an exothermic reaction commences at 90° C. In this exothermic reaction, 290 J/g of heat are liberated between 90° and 200° C. and two maximum values are observed, namely at 140° and 163° C. This mixture has the following gel times.
110 s at 200° C.
270 s at 180° C.
630 s at 160° C.
The mixture is cured for 4 hours at 180° C., to give a clear casting with a glass transition temperature (DSC) of 164° C.

A₂) 10 parts of the hardener prepared in accordance with Example 2 are mixed with 90 parts of bisphenol A diglycidyl ether (epoxy value: 5.4 eq/kg). When this mixture is heated, an exothermic reaction commences at 150° C. In this exothermic reaction, 320 J/g of heat are liberated between 105° and 210° C. and two maximum values are observed, namely at 152° and 178° C. This mixture has the following gel times:
115 s at 200° C.
350 s at 180° C.
1140 s at 160° C.
The mixture is cured for 4 hours at 180° C., to give a clear yellowish casting with a glass transition temperature of 167° C.

A₃) 10 parts of the hardener prepared in accordance with Example 4 are mixed with 90 parts of bisphenol A diglycidyl ether (epoxy value: 5.4 eq/kg). When this mixture is heated, an exothermic reaction commences at 90° C. In this exothermic reaction, 370 J/g of heat are liberated between 145° and 171° C. and two maximum values are observed, namely at 145° and 171° C. This mixture has the following gel times:
135 s at 200° C.
270 s at 180° C.
780 s at 160° C.
The mixture is cured for 4 hours at 180° C., to give a clear yellowish casting with a glass transition temperature (DSC) of 158° C.

A₄) 15 parts of the hardener prepared in accordance with Example 5 are mixed with 85 parts of bisphenol A diglycidyl ether (epoxy value: 5.4 eq/kg). This mixture gels at 170° C. in 900 s. Addition of 0.2 part of 2-ethylimidazole reduces the gel time to 120 s. Clear, yellowish castings with a glass transition temperature of 165° C. are obtained by curing the mixtures for 4 hours at 180° C.

A₅) 10 parts of the hardener prepared in accordance with Example 6 are mixed with 90 parts of bisphenol A diglycidyl ether (epoxy value: 5.4 eq/kg) and 0.5 part of 2-ethylimidazole. When this mixture is heated, an exothermic reaction commences at 90° C. A clear, yellowish casting with a glass transition temperature (DSC) of 154° C. is obtained by curing this mixture for 4 hours at 180° C.

A₆) 10 parts of the hardener prepared in accordance with Example 5 are mixed with 90 parts of bisphenol A digylcidyl ether (epoxy value: 5.4 eq/kg) and 0.5 part of 2-ethylimidazole and the mixture is cured for 1 hour at each of the following temperatures: 150° C., 160° C. and 190° C. Clear, yellow castings with the following properties are obtained:
glass transition temperature (DSC): 150° C.
flexural strength (ISO 178): 119 N/mm
edge fibre elongation (ISO 178): 5.9%
impact strength (ISO/R 179): 22.9 kJ/m²
cold water absorption (4 days): 0.30%
boiling water absorption (1 h): 0.30%
weight loss (−5%): 325° C.
(−10%): 360° C.

What is claimed is:
1. An oligomeric cyanoguanidine of formula I

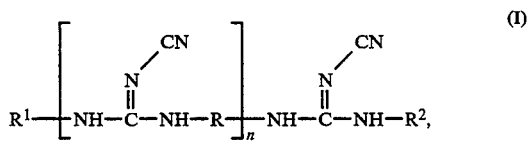

wherein
R is a divalent $C_2$–$C_{20}$aliphatic hydrocarbyl, mono- or polynuclear $C_5$–$C_{20}$cycloaliphatic, $C_6$–$C_{20}$ aromatic radical; or
R is a divalent radical of furan, pyran, pyridine, pyrrole, imidazole or thiophene; or
R is a group of formula II

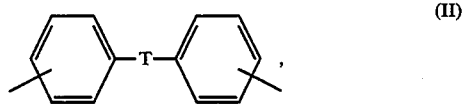

wherein
T is methylene, isopropylidene, CO, O, S or $SO_2$;
$R^1$ and $R^2$ are each independently of the other $C_1$–$C_{12}$alkyl, $C_5$–$C_{10}$cycloalkyl, $C_6$–$C_{10}$aryl, $C_7$–$C_2$aralkyl or a monovalent radical of furan, pyran, pyridine, pyrrole, imidazole or thiophene; and,
n is an integer from 1 to 20,
which radicals R, $R^1$ and $R^2$ are unsubstituted or are substituted by $C_1$–$C_4$alkyl, $C_1$–$C_4$alkoxy, nitro, halogen, $R^3$OCO or $R^3$COO, where $R^3$ is phenyl or $C_1$–$C_4$alkyl,
with the proviso that 1,6-hexane-bis(3-cyano-2-isobutylguanidine) is excluded.

2. A cyanoguanidine according to claim 1, wherein n is an integer from 1 to 10.

3. A cyanoguanidine according to claim 1, wherein R is an aliphatic radical of 2 to 10 carbon atoms, a cycloaliphatic radical of 5 or 6 carbon atoms or an aromatic radical of 6 to 10 carbon atoms, or is a group of formula II, wherein T is methylene or isopropylidene.

4. A cyanoguanidine according to claim 1, wherein $R^1$ and $R^2$ are each independently of the other $C_1$–$C_6$alkyl, $C_5$–$C_6$cycloalkyl, $C_6$–$C_{10}$aryl or benzyl.

5. A cyanoguanidine according to claim 1, wherein R is phenylene, methylphenylene, the radical

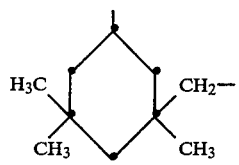

or a group of formula II, wherein T is methylene, and $R^1$ and $R^2$ are each independently of the other phenyl, tolyl, methoxyphenyl, naphthyl or cyclohexyl.

6. A cyanoguanidine according to claim 1, wherein R, $R^1$ and $R^2$ are $C_6$-$C_{10}$aryl or $C_7$-$C_{12}$aralkyl radicals.

7. A cyanoguanidine according to claim 1, wherein R is methylphenylene or a group of formula II, in which T is methylene, and $R^1$ and $R^2$ are each phenyl.

8. A mixture of cyanoguanidines obtainable by heating a mixture containing a monoisocyanate $R^1$—NCO and/or $R^2$—NCO and a diisocyanate OCN—R—NCO, in the prescence of a catalyst, to give a carbodiimide or formula III*

wherein $R^1$, $R^2$ and R are as defined in claim 1 and n* is 0 or an integer from 1 to 20, and subsequently reacting said carbodiimide of formula III* with cyanamide.

* * * * *